(12) United States Patent
Shaban

(10) Patent No.: US 9,844,628 B1
(45) Date of Patent: Dec. 19, 2017

(54) SYSTEM AND METHOD FOR CONTROLLING A SELF-INJECTOR DEVICE

(71) Applicant: Kavan J. Shaban, Bethesda, MD (US)

(72) Inventor: Kavan J. Shaban, Bethesda, MD (US)

( * ) Notice: Subject to any disclaimer, the term of this patent is extended or adjusted under 35 U.S.C. 154(b) by 127 days.

(21) Appl. No.: 14/703,675

(22) Filed: May 4, 2015

Related U.S. Application Data

(63) Continuation of application No. 13/103,010, filed on May 6, 2011, now Pat. No. 9,022,988.

(60) Provisional application No. 61/332,670, filed on May 7, 2010.

(51) Int. Cl.
| | | |
|---|---|---|
| A61M 5/172 | (2006.01) | |
| A61M 5/20 | (2006.01) | |
| A61M 5/145 | (2006.01) | |
| A61M 5/24 | (2006.01) | |

(52) U.S. Cl.
CPC ............ *A61M 5/20* (2013.01); *A61M 5/1454* (2013.01); *A61M 5/24* (2013.01); *A61M 2205/27* (2013.01); *A61M 2205/3576* (2013.01); *A61M 2205/50* (2013.01); *A61M 2205/581* (2013.01); *A61M 2205/582* (2013.01); *A61M 2205/583* (2013.01); *A61M 2205/60* (2013.01)

(58) Field of Classification Search
CPC ...... A61M 2205/50; A61M 2205/6072; A61M 2205/6018; A61M 2205/609; A61M 2205/702; A61M 5/172; A61M 2205/60; A61M 2205/6009
See application file for complete search history.

(56) References Cited

U.S. PATENT DOCUMENTS

| | | |
|---|---|---|
| 3,516,577 A | 6/1970 | Pitt |
| 4,668,218 A | 5/1987 | Virtanen |
| 4,760,939 A | 8/1988 | Ball et al. |
| 4,815,632 A | 3/1989 | Ball et al. |
| 4,850,966 A | 7/1989 | Grau et al. |
| 5,097,834 A | 3/1992 | Skrabal |
| 5,104,380 A | 4/1992 | Holman et al. |
| 5,243,982 A | 9/1993 | Mostl et al. |
| 5,284,133 A | 2/1994 | Burns et al. |
| 5,300,030 A | 4/1994 | Crossman et al. |
| 5,308,341 A | 5/1994 | Chanoch |

(Continued)

OTHER PUBLICATIONS

Delivering Injectables: Devices & Device Components, pp. 1-20, ONdrugDelivery Ltd, United Kingdom, 2007.

(Continued)

*Primary Examiner* — Kevin C Sirmons
*Assistant Examiner* — Deanna K Hall
(74) *Attorney, Agent, or Firm* — David C. Isaacson; Fitzgerald & Isaacson, LLP

(57) ABSTRACT

A cartridge-based computer controlled self-injection device automatically regulates time and dosage administered to a patient. Cartridges can be electronically tagged so the injection device can determine the content, volume, expiration date, and physician prescribed dosage timetable. Authentication verifies the device and ensures the proper patient is using the device with the appropriate therapeutic injectant. Authentication further provides information controlling device operation including expiration dates and clock synchronization. Therapeutic injectant administration statistics, such as date and time of administration of a therapeutic injectant are stored and provide to a health care provider for monitoring. Patients can be notified of nearing or missed administrations.

20 Claims, 2 Drawing Sheets

(56) References Cited

U.S. PATENT DOCUMENTS

| | | | |
|---|---|---|---|
| 5,391,157 A | 2/1995 | Harris et al. |
| 5,536,249 A | 7/1996 | Castellano et al. |
| 5,554,125 A | 9/1996 | Reynolds |
| 5,720,733 A | 2/1998 | Brown |
| 5,728,074 A | 3/1998 | Castellano et al. |
| 5,782,814 A | 7/1998 | Brown et al. |
| 5,845,264 A | 12/1998 | Nellhaus |
| 5,925,021 A | 7/1999 | Castellano et al. |
| 5,928,205 A | 7/1999 | Marshall |
| 6,071,272 A | 6/2000 | Hoffman et al. |
| 6,110,148 A | 8/2000 | Brown et al. |
| 6,113,578 A | 9/2000 | Brown |
| 6,142,339 A | 11/2000 | Blacker et al. |
| 6,146,361 A | 11/2000 | DiBiasi et al. |
| 6,159,181 A | 12/2000 | Crossman et al. |
| 6,161,724 A | 12/2000 | Blacker et al. |
| 6,200,296 B1 | 3/2001 | Dibiasi et al. |
| D446,579 S | 8/2001 | Perthu |
| 6,277,099 B1 | 8/2001 | Strowe et al. |
| 6,287,283 B1 | 9/2001 | Ljunggreen et al. |
| 6,352,523 B1 | 3/2002 | Brown et al. |
| 6,435,372 B1 | 8/2002 | Blacker et al. |
| 6,454,746 B1 | 9/2002 | Bydlon et al. |
| 6,482,186 B1 | 11/2002 | Douglas et al. |
| 6,562,011 B1 | 5/2003 | Buch-Rasmussen et al. |
| 6,582,408 B1 | 6/2003 | Buch-Rasmussen et al. |
| 6,589,210 B1 | 7/2003 | Rolfe |
| 6,589,229 B1 | 7/2003 | Connelly et al. |
| 6,605,065 B1 | 8/2003 | Tarentino |
| 6,645,171 B1 | 11/2003 | Robinson et al. |
| 6,648,859 B2 | 11/2003 | Bitdinger et al. |
| 6,656,159 B2 | 12/2003 | Flaherty |
| 6,699,218 B2 | 3/2004 | Flaherty et al. |
| 6,740,059 B2 | 5/2004 | Flaherty |
| 6,749,587 B2 | 6/2004 | Flaherty |
| 6,768,425 B2 | 7/2004 | Flaherty et al. |
| 6,814,265 B2 | 11/2004 | Clifford et al. |
| 6,926,002 B2 | 8/2005 | Scarrott et al. |
| 6,932,793 B1 | 8/2005 | Marshall et al. |
| 6,997,349 B2 | 2/2006 | Blacker et al. |
| 7,025,098 B2 | 4/2006 | Osborne |
| 7,029,455 B2 | 4/2006 | Flaherty |
| 7,066,907 B2 | 6/2006 | Crossman et al. |
| 7,137,964 B2 | 11/2006 | Flaherty |
| 7,143,908 B2 | 12/2006 | Blacker et al. |
| 7,144,384 B2 | 12/2006 | Gorman et al. |
| 7,191,916 B2 | 3/2007 | Clifford et al. |
| 7,291,132 B2 | 11/2007 | DeRuntz et al. |
| 7,311,879 B2 | 12/2007 | Hodson |
| 7,404,796 B2 | 7/2008 | Ginsberg |
| 7,416,540 B2 | 8/2008 | Edwards et al. |
| 7,427,275 B2 | 9/2008 | DeRuntz et al. |
| 7,455,663 B2 | 11/2008 | Bikovsky |
| 7,495,546 B2 | 2/2009 | Lintell |
| 7,498,563 B2 | 3/2009 | Mandro et al. |
| 7,544,188 B2 | 6/2009 | Edwards et al. |
| 7,563,252 B2 | 7/2009 | Marshall et al. |
| 7,575,130 B2 | 8/2009 | Blacker et al. |
| 7,591,801 B2 | 9/2009 | Brauker et al. |
| 7,614,545 B2 | 11/2009 | Christoffersen et al. |
| 7,621,273 B2 | 11/2009 | Morton et al. |
| 7,648,482 B2 | 1/2010 | Edwards et al. |
| 7,648,483 B2 | 1/2010 | Edwards et al. |
| 7,668,731 B2 | 2/2010 | Martucci et al. |
| 7,682,338 B2 | 3/2010 | Griffin |
| 7,695,453 B2 | 4/2010 | Marshall et al. |
| 7,698,156 B2 | 4/2010 | Martucci et al. |
| 7,699,833 B2 | 4/2010 | Moberg et al. |
| 7,704,237 B2 | 4/2010 | Fisher et al. |
| 8,209,060 B2 | 6/2012 | Ledford |
| 2003/0140929 A1 | 7/2003 | Wilkes et al. |
| 2005/0178795 A1 | 8/2005 | Inoue |
| 2006/0218011 A1 | 9/2006 | Walker et al. |
| 2007/0090126 A1 | 4/2007 | Tanaka et al. |
| 2008/0015503 A1 | 1/2008 | Jansen et al. |
| 2008/0110924 A1 | 5/2008 | Fueki et al. |
| 2008/0236301 A1 | 10/2008 | Fukushima et al. |
| 2008/0262469 A1 | 10/2008 | Brister et al. |
| 2008/0306434 A1 | 12/2008 | Dobbles et al. |
| 2008/0306435 A1 | 12/2008 | Kamath et al. |
| 2008/0306436 A1 | 12/2008 | Edwards et al. |
| 2008/0306444 A1 | 12/2008 | Brister et al. |
| 2009/0068066 A1 | 3/2009 | Hoffman et al. |
| 2010/0049126 A1 | 2/2010 | Bronfeld et al. |

OTHER PUBLICATIONS

Delivering Injectables: Formulations, Auto-Injectors and Needle-Free, pp. 1-24, ONdrugDelivery Ltd, United Kingdom, 2008.
Drug Delivery in Diabetes: Making Effective Treatment Tolerable, pp. 1-20, ONdrugDelivery Ltd, United Kingdom, 2006.
Injectable Drug Delivery 2010: Devices Focus, pp. 1-20, Frederick Furness Publishing, United Kingdom, 2010.
Prefilled Syringes: The Trend for Growth Strengthens, pp. 1-32, ONdrugDelivery Ltd, united Kingdom, 2006.
Prefilled Syringes: Innovations that Meet the Growing Demand, pp. 1-28, ONdrugDelivery Ltd, United Kingdom, 2005.
Prefilled Syringes: Device Suppliers Meeting Pharmaceutical Standards, pp. 1-28, ONdrugDelivery Ltd, United Kingdom, 2007.
Prefilled Syringes: The Container of Choice for Today's Injectables, pp. 1-23, ONdrugDelivery Ltd, United Kingdom, 2008.
Prefilled Syringes: Innovation, Validation, Regulation, pp. 1-32, ONdrugDelivery Ltd, United Kingdom, 2009.
Prefilled Syringes: New Ideas for the New Decade, pp. 1-24, ONdrugDelivery United Kingdom, 2010.
Delivering Injectables: Safety, Efficancy and Convenience in Today's Complex Market, pp. 1-20, ONdrugDelivery Ltd, United Kingdom, 2005.
Safer Injections: Reducing Risk for Nurses, Physicians and Patients Alike, pp. 1-28, ONdrugDelivery Ltd, United Kingdom, 2005.
Thompson, Ian, New Generation Auto-Injectors: Taking Self Injection Beyond Prefilled Syringes, pp. 1-4, ONdrugDelivery Ltd, United Kingdom, 2005.
The Medical House, http://www.themedicalhouse.com/needle_free_injectors.asp, webpage, Consort Medical plc, 2008.
Prefilled Syringes: The Container of Choice for Today's Injectables, pp. 1-2, 24-44, ONdrugDelivery Ltd, United Kingdom, 2008.
Office Action dated Aug. 13, 2014 in U.S. Appl. No. 13/103,010, filed May 6, 2011.
Office Action dated Feb. 28, 2014 in U.S. Appl. No. 13/103,010, filed May 6, 2011.

SYSTEM AND METHOD FOR CONTROLLING A SELF-INJECTOR DEVICE

This application is a continuation of U.S. patent application Ser. No. 13/103,010, filed May 6, 2011 (pending), which claims the benefit of U.S. Provisional App. No. 61/332,670 filed May 7, 2010, each of which is hereby incorporated by reference in its entirety.

BACKGROUND

Technical Field

Embodiments of the present invention relate generally to medical devices for administering medications, vitamins, hormones, and other therapeutics that are administered via injection. More specifically, embodiments of the present invention relate to a programmable self-injector device.

Background

Modern patient care strives to place patients in more control of their health care. One movement, for example, seeks to give patients control over their health care data. For example, systems such as Microsoft HealthVault® and Google Health, among others, allow patients to store their health care records in patient-accessible electronic medical records. Thus, patients will have access to their health care records when they need them, such as when they change physicians.

In this same vein, it would be advantageous to allow patients to take more control over administration of their health care. Such self-administration would relieve patients from frequent and often inconvenient trips to health care service providers' offices. While most people can administer medications, in oral form, such as liquids, pills, capsules, and tablets with little difficulty, the same is not generally true of medicinal administrations requiring injections. Whether fear of needles or insecurity in drawing required dosages or proper injection technique, most people are not comfortable administering medications requiring injections to themselves.

For example, in the typical clinical setting, therapeutic injectants delivered via intra-muscular, subcutaneous, and other site injections is extremely commonplace to treat numerous diseases, including diabetes, hormone deficiency, and obesity. Typically, these injection-based therapies require administration in regulated dosages. In some cases, not only must the dosages be regulated, but the timetables for administering the therapy can be quite complex. Thus, patient self-injection presents myriad problems in a clinical setting. If left responsible for his or her own injection, a patient may not adhere to a prescribed timetable, or may forget the injection entirely. Even where the patient remembers to inject himself or herself, the patient may administer either too high a dosage or too low a dosage.

Not only are there patient-centric concerns, but many physicians are reluctant to allow patients to administer their own medications or other therapeutic injectants via injection because there is no viable way to monitor patient compliance with prescribed dosages and timetables. In essence, the physician does not know whether the patient administered the correct dosage or took the medication at all. As a result, all but the most trivial therapies fall outside the realm of patient self-injection.

In summary then, at least two issues obstruct widespread implementation of patient self-injection for treatment of advanced diseases: (1) Correct regulation of the amount (dose) of injectable medicine; and (2) ensuring compliance with the timetable for the injection as prescribed by the physician.

SUMMARY

In an embodiment, a cartridge-based computer controlled self-injection device automatically regulates time and dosage administered to a patient.

Cartridges can be electronically tagged so the injection device can determine the content, volume, expiration date, and physician prescribed dosage timetable.

Authentication verifies the device and ensures the proper patient is using the device with the appropriate therapeutic injectant. Authentication further provides information controlling device operation including expiration dates and clock synchronization.

Therapeutic injectant administration statistics, such as date and time of administration of a therapeutic injectant, are stored and provide to a health care provider for monitoring. Patients can be notified of nearing or missed administrations.

In an embodiment, an injection device to perform an injection of an injectant, such as a therapeutic injectant, to a patient includes a plunger to cause the injectant to be injected into a patient, a receiver to receive information, and a microprocessor to control the injection using the information.

In another embodiment, a method for controlling an injection device includes receiving information concerning the injection and controlling a plunger to inject an injectant into a patient using the information.

DETAILED DESCRIPTION

Figure 1:
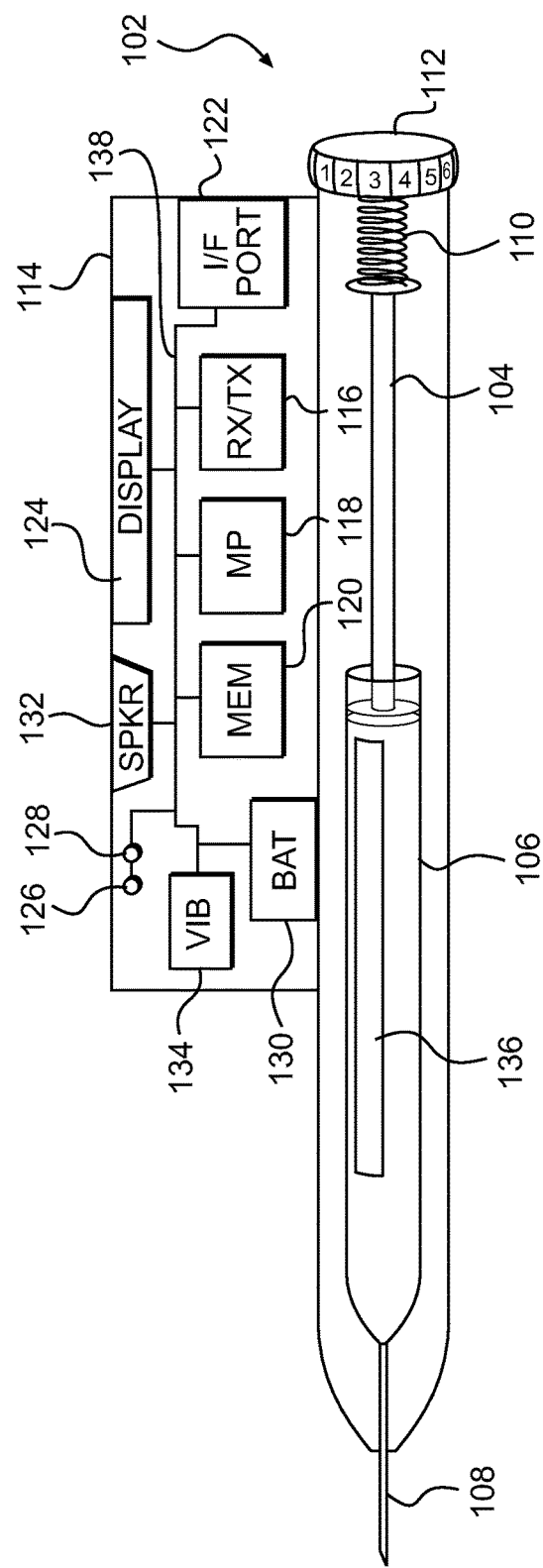
FIG. 1 is a schematic diagram of an injection device according to an embodiment of the present invention.

FIG. 1 is a schematic diagram of an injection device according to an embodiment of the present invention. An injection device 102 includes a plunger 104 movably attached to device 102. Plunger 104 engages a cartridge 106 having therein a therapeutic injectant to be injected into a patient through a needle 108. Therapeutic injectants include medicines, vitamins, hormones, or other therapeutics that are administered to a patient by injection.

A spring 110 attached to plunger 104 causes plunger 104 to move longitudinally along device 102 to eject the therapeutic injectant from cartridge 106. The amount plunger 104 moves determines the dosage administered to the patient. To control the amount of movement of plunger 104, the patient rotates a dosage control 112. Dosage control 112 causes spring 110 to recoil by an amount proportional to the desired dosage, whereupon spring 110 is held retracted until released. When the spring 110 is released, spring 110 forces plunger 104 to move longitudinally along injection device 102, thereby expelling injectant from cartridge 106 through needle 108. In an embodiment, needle 108 is retractable when not in use. Such automatic injection devices are well-known, and available for example, from Owen Mumford of Oxford, England.

Injection device 102 further includes a compartment 114. Compartment 114 houses a receiver/transmitter 116, a microprocessor 118, and a memory 120. Microprocessor 118 can be any processor or controller configured to control device 102 as described herein. In an embodiment, compartment 114 includes an interface port 122, such as a USB port or other interface through which data can be transferred. In an embodiment, compartment 114 includes a display screen 124. Injection device 102 uses display screen 124 to communicate information to the patient. For example, in an embodiment, display screen 124 can display the next dosage date and time, how many dosages are left until the next cartridge change and any error conditions or faults that may occur.

In an embodiment, compartment 114 includes at least one indicator lamp 126 and 128. The indicator lamp can be different colors. For example, in an embodiment, there are two indicator lamps, one red and one green. In an embodiment, compartment 114 includes a speaker 132. In embodiment, compartment 114 includes a vibration mechanism 134. Compartment 114 also includes a battery 130 or other power source. Battery 130 can be rechargeable. In an embodiment, battery 130 serves as vibration device 134. In an embodiment, components are coupled via a bus 138. In an embodiment, bus 138 provides data communication between components. In an embodiment, bus 138 carries power from battery 130 to those components requiring power. In an alternative embodiment, power is supplied to components through a common backplane.

In operation, a health care provider sends one or more control signals to injection device 102 to control its operation. The control signals are received by a receiver portion of receiver/transmitter 116. The control signals may control various modes of operation of injection device 102. For example, in an embodiment, the control signals include dosage amount and dosage timetable. Other control signals may be included as required for a particular implementation. For example, device information, authentication controls, and other information may be included in control signals sent from the health care provider.

It should be noted that receiver/transmitter 116 can be a single unit having both a receiver and transmitter. Alternatively, receiver/transmitter 116 may comprise a separate receiver unit and a separate transmitter unit.

In an embodiment, receiver/transmitter 116 processes over-the-air signals. For example, in an embodiment, receiver/transmitter 116 receives signals adhering to the Bluetooth or the 802.11 set of communication standards. Other communication standards could be used as would be well-known to those skilled in the art.

In another embodiment, receiver/transmitter 116 processes signals received on wires or through a docking station. For example, in an embodiment, injection device 102 can connected to a computer via an interface port such as interface port 122. Interface port can be, for example, a USB port of other interface through which data can be transferred. In another embodiment, interface port 122 allows connecting injection device 102 to a docking station. Other connection mechanisms would be apparent to those skilled in the art. In an embodiment, the control signals can be received over the Internet or other computer network.

In an embodiment, the control signals initially authenticate injection device 102. As part of the authentication, injection device 102 is verified with the health care provider. In an embodiment, the verification is performed using well-known public-private key encryption message exchange to confirm that injection device 102 is a valid injection device for the health care provider.

Another aspect of authentication is clock synchronization. In clock synchronization, a clock internal to injection device 102 is synchronized with a clock at the health care provider server to be used to ensure proper adherence to the prescribed administration timetable. For example, in an embodiment, the current time provided by the health care provider server is sent to injection device 102 during authentication.

In addition, during authentication, injection device 102 receives information concerning therapeutic injectants. For example, in an embodiment, this information includes the names of therapeutic injectants the patient is currently prescribed to take, prescribed dosages corresponding to those therapeutic injectants, and prescribed timetables for administering the therapeutic injectants. In an embodiment, the information is encrypted prior to being sent to injection device 102.

In addition, as described below, during authentication, injection device 102 can upload data concerning one or more previous injections to the health care service provider servicer. In an embodiment, the data is encrypted prior to being uploaded.

Control signals received by device 102 are processed by microprocessor 118. Microprocessor 118 operates according to a program stored in memory 120. Memory 120 also acts as a scratch pad memory for use by microprocessor 118 during its operation.

Memory 120 can also store patient data and injection data. For example, in an embodiment, the patient data includes the patient's name, a unique patient identifier, medicines or other therapeutic injectants that are currently prescribed to the patient, dosages corresponding to the medicines or other therapeutic injectants that are currently prescribed to the patient, the timetable for administering medicines or other therapeutic injectants that are currently prescribed to the patient, and any other data that may be desired for a particular implementation. In an embodiment, the injection data includes the date of an injection, the dosage of an injection, and any other injection data desired for a particular implementation. The injection data can be reset after uploading to a health care provider as described below. In another embodiment, a separate memory stores patient data and injection data.

Memory 120 can also store injection device data including, without limitation, a unique device identification for injection device 102 and a public/private key pair to be used in injection device authentication. In another embodiment, a separate memory can be used to store the unique device identification for injection device 102.

The program stored in memory 120 can be preinstalled by a manufacturer of injection device 120 or third party manufacturer. Further, the program stored in memory 120 may be sent in the control signals received by receiver/transmitter 116 or uploaded via interface port 122.

Control signals sent by the health provider can include a prescribed dosage amount. The program stored in memory 120 configures injection device 102 to inject the amount indicate by the dosage amount receive in the control signals. In an embodiment, the dosage amount is indicated on display screen 124 to the patient. The patient sets injection device 102 to administer the dosage indicated on display screen 124 using dosage control 112.

In an embodiment, the program executing on microprocessor 118 verifies that dosage control 112 has been set to the correct setting to administer the dosage indicated on display screen 124. If the dosage setting of dosage control 112 is correct, an indication can be provided to the patient. Such indication can be visual. For example, in an embodiment, a lamp 126 of a first color is lit to indicate injection device 102 is ready to administer the injection. In an embodiment, the indication is audible. For example, in an embodiment, a first beep or a first message can be provided via speaker 132. In an embodiment, the indication is tactile, for example by causing vibrating mechanism 134 to vibrate. Any combination of visual, audible, and tactile indications can be used in an embodiment.

If the dosage setting of dosage control 112 is incorrect, an indication can be provided to the patient. Such indication can be visual. For example, in an embodiment, a lamp 126 of a second color is lit to indicate injection device 102 is ready to administer the injection. In an embodiment, the indication is audible. For example, in an embodiment, a second beep or a second message can be provided via speaker 132. In an embodiment, the indication is tactile, for example by causing vibrating mechanism 134 to vibrate. Any combination of visual, audible, and tactile indications can be used in an embodiment. In an embodiment, injection device 102 is disabled if not set properly.

In an alternate embodiment, a computer-controlled actuator automatically configures dosage control 112 to administer the dosage amount indicated on display screen 124. For example, in an embodiment, microprocessor 118 causes the actuator to rotate dosage control 112 by an amount sufficient to cause spring 110 to move plunger 104 to cause the proper amount of injectant to be administered to the patient. When injection device has been properly configured, an indication can be provided to the patient. Such indication can be visual. For example, in an embodiment, a lamp 126 is lit to indicate injection device 102 is ready to administer the injection. In an embodiment, the indication is audible. For example, in an embodiment, beep or a message can be provided via speaker 132. In an embodiment, the indication is tactile, for example by causing vibrating mechanism 134 to vibrate. Any combination of visual, audible, and tactile indications can be used in an embodiment.

After the medicine or other injectant is administered, injection device 102 uploads data back to the health care provider concerning the injection through the transmitter of receiver/transmitter 116. The data can include any data desired by the health care provider. For example, in an embodiment, the data includes the name of the patient, the name of the therapeutic injectant administered, the dosage administered, and the date and time of the administration.

In an alternate embodiment, after the medicine or other injectant is administered, injection device 102 stores the data concerning the injection in memory 120 or other memory for later uploading to the health care provider server. For example, the data can be uploaded to the heath care provider server at a prescheduled time or the next time injection device 102 is authenticated with the health care service provider. As described above, the health care provider can be notified that the data has been uploaded.

The uploaded data can be stored in an electronic medical record associated with the patient. The health care provider can review the uploaded data to ensure the patient is complying with any prescribed therapy regimen. In an embodiment, the health care provider is notified that the data has been uploaded. The physician notification can be in any of a number of ways, including without limitation, electronic mail, text message, telephone call, voice message, facsimile, page. The notification can include any combination of notification mechanisms.

In an embodiment, cartridge 106 is marked with an electronically readable marking or tag 136, for example, via RFID tag, magnetic strip, polymer strip, or other electronic marking. According to an embodiment, device 102 reads electronically readable marking 136 to determine information about cartridge 106. For example, the marking may include the name of the therapeutic injectant, the expiration date of the injectant, the volume of the therapeutic injectant contained in cartridge 106, the prescribed dosage, and the prescribed timetable for administering the medication or other therapeutic injectant. Any additional information can be included on electronically readable marking 136, including without limitation, the patient's name, the unique number of injection device 102.

In an embodiment, the program executing on microprocessor 118 reads the patient's name from electronically readable marking 136 and compares it to the name in the patient data stored in memory 120 or other memory. If the names match, injection device 102 can be used to administer the therapeutic injectant.

If the names do not match, the patient is notified. For example, the patient notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

Further, if the names do not match, in an embodiment, injection device 102 is disabled. Disabling device 102 when the patient's name does not match the name associated with the therapeutic injectant to prevent the patient from using an invalid cartridge.

In an embodiment, the program executing on microprocessor 118 reads the name of the therapeutic injectant from electronically readable marking 136 and compares it to the names of the medicines or other therapeutic injections stored in memory 120 or other memory. If the read medicine or therapeutic injectants matches one of the stored medicines or other therapeutic injectants, injection device 102 can be used to administer the therapeutic injectant.

If the read medicine or therapeutic injectants does not match one of the stored medicines or other therapeutic injectants, the patient is notified. For example, the patient notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

Further, if the read medicine or therapeutic injectants does not match one of the stored medicines or other therapeutic injectants, in an embodiment, injection device 102 is disabled. Disabling device 102 when the read medicine or therapeutic injectants does not match one of the stored medicines or other therapeutic injectants prevents the patient from using an invalid cartridge.

In an embodiment, the program executing on microprocessor 118 reads the expiration date from electronically readable marking 136 to the current date to determine if the expiration date of cartridge 106 has passed. If the expiration date has not passed, injection device 102 can be used to administer the therapeutic injectant.

If the expiration date of cartridge 106 has passed, the patient is notified. For example, the patient notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

Further, if the expiration date of cartridge 106 has passed, in an embodiment, injection device 102 is disabled. Disabling device 102 when the expiration date of cartridge 106 has passed prevents the patient from using an expired cartridge.

In an embodiment, the program executing on microprocessor 118 also ensures that the patient adheres to the prescribed timetable for administering therapeutic injectants. That is, based on the timetable information provided to injection device 102, the program determines the time of each next injection. Injection device 102 can display next times for injection to patient on display screen 124.

The program executing on microprocessor 124 also monitors the dosage and time of each administration of a therapeutic injectant. Injection device 102 can notify the patient that an administration time is approaching. The time prior to providing the notification can be set by the manufacture or configured by the patient. The notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

Further, if a patient misses a prescribed administration time, the patient is notified of the missed administration. The notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

Injection device 102 can also enhance medical compliance measures by ensuring that all cartridges are returned to ensure any unused medicine is not properly siphoned for non-prescription uses. For example, when a cartridge is completely consumed, its unique identification is sent back to the health care provider. Injection device 102 can be disabled until all spent cartridges are returned.

Injection device 102 can be reprogrammed with a different dosage and/or timetable while it still houses a cartridge. This would be extremely useful in allowing the physician to modulate therapy mid-stream in treatment so as to aid the patient in attaining better results. An alarm is provided to the patient if there is insufficient injectant in the cartridge to comply with the new regimen. As described above, the alarm can be visual, audible, and/or tactile. An alarm is also provided to the doctor so that he or she can take corrective action. For example, the doctor might adapt the regimen to use the remaining injectant.

Therapeutic injectants may require shaking prior to being administered. In such a case, the information included in electronically readable tag 136. If upon reading electronically readable tag 136, microprocessor 118 determines that the therapeutic injectant requires shaking prior to administration, the patient will be notified. The notification can be visual. For example, in an embodiment, a lamp 126 is lit to notify the patient or a message is displayed to the patient on display screen 124. In an embodiment, the patient notification is audible. For example, in an embodiment, beep or a message can be provided via speaker 132. In an embodiment, the notification is tactile, for example by causing vibrating mechanism 134 to vibrate. Any combination of visual, audible, and tactile patient notification can be used in an embodiment.

In an embodiment, display screen 124 and/or speaker 132 instructs the patient that injection device 102 must be shaken at least a predetermined number of times. Injection device 102 detects whether the patient has shaken injection device 102 the requisite number of times. For example, in an embodiment, an accelerometer is used to detect shaking. Microprocessor 118 interprets the signal output by the accelerometer to determine if the patient has shaken device 102 the requisite number of times. If so, injection device 102 is enable to administer the therapeutic injectant. If not, injection device 102 is disabled, and a message is provided to the patient either audibly through speaker 132 or visually on display screen 124 that additional shaking is required. Once the patient has sufficiently shaken injection device 102, it is enabled to allow administration of the therapeutic injectant.

The device may also come in a multi-cartridge design. The multi-cartridge design would enable the delivery of different therapeutic injectants under one controlling prescription mechanism. This would be extremely useful when the physician would like the patient to dose with certain medications in the morning and different medications in the evening.

In an embodiment for example, device 102 includes a carousel having a plurality of cartridges. A microprocessor can control the carousel to automatically rotate to the appropriate cartridge depending on which therapeutic injectant is required at a particular time.

In another embodiment, a patient may be prescribed to receive several injectants at a given time. In that case, the microprocessor can control the carousel to provide each required cartridge in turn, and then rotate to the next cartridge when a particular injection is complete. The patient can be notified when all injections are complete.

Alternate form factors can be used to house the microprocessor based control and the cartridges. For example, a rectangular or other geometric shape form factor can be used.

In summary, an embodiment provides at least the following advantages over conventional self-injection devices: (1) automatic regulation of the correct amount of injectable medicine, (2) automatic compliance to a physician prescribed dosage medicine, (3) automatic reporting back to the physician of actual dosage times, (4) automatic detection of only the correct injectable medication for the prescribed patient, (5) automatic enforcement of medicinal expiration dates, and (6) multi-medicinal delivery platform.

Figure 2:
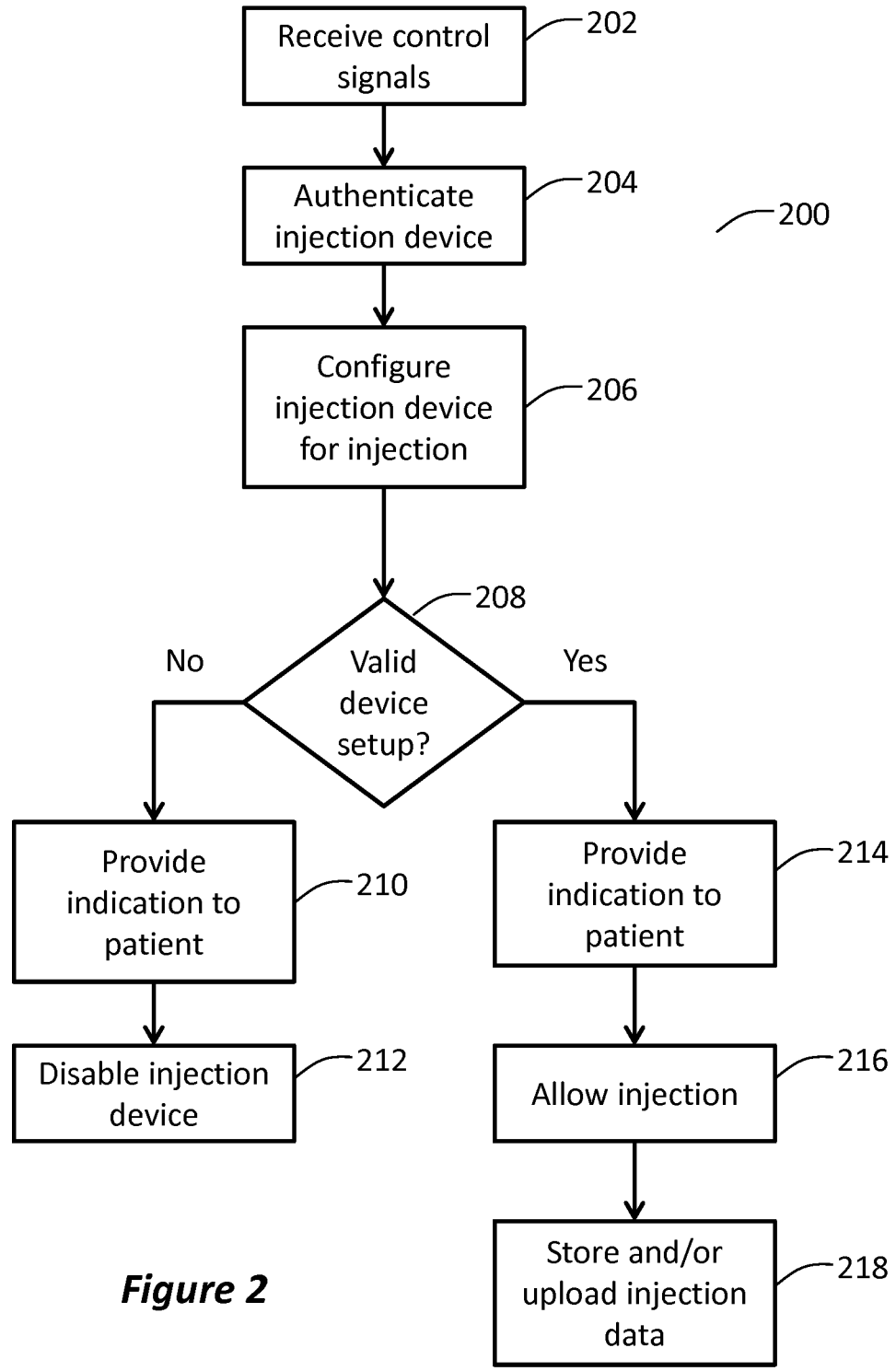
FIG. 2 is a flow chart of a method for a controlling a self-injector device according to an embodiment.

FIG. 2 is a flow chart 200 for a controlling a self-injector device according to an embodiment. In an embodiment, the process depicted in the flow chart and accompanying text is executed in microprocessor 118. One or more control signals as described above are received in step 202. In step 204, the injection device is authenticated. For example, in an embodiment, the authentication process includes verification that the injection device is a valid device, synchronization with the health care provider clock, receipt of information concerning the therapeutic injectant for verification purposes, and uploading of information associated with previously stored injection data. Other authentication tasks can be performed if desired in step 204.

In step 206, the device is configured for an injection. For example, in an embodiment, this includes providing instructions to the patient concerning setting the injection device or automatically setting the injection device. Other device configurations and/or instructions can be provided in step 206.

In step 208, the injection device settings are validated to ensure the injection device is properly configured for a particular injection. For example, in an embodiment, patient identify is verified, therapeutic injectant is verified, expiration date is verified, dosage amount is verified, and dosage time is verified. Other verifications can take place in step 208.

If the injection device is no properly set up, processing continues in step 210, wherein the patient is notified of the improper set up. The device is disabled in step 212. If the patient can fix the problem, the device will so prompt the patient and then return to step 208 for revalidation of the injection device configuration.

If the injection device was determined to be properly configured in step 208, processing continues in step 214, where the patient is notified that the configuration is proper and that he or she may proceed with the injection. In step 216, the injection device is configured to allow the injection. In step 218, injection data associated with the injection is stored in memory and/or uploaded to the health care provider.

The foregoing disclosure of the preferred embodiments of the present invention has been presented for the purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may by varied and still remain within the spirit and scope of the present invention.

What is claimed is:

1. A method for controlling an injection device, comprising:
receiving, via a receiver located in the injection device, control signals that include information concerning an injection, wherein the information includes a time of day when the injection is scheduled to be performed;
monitoring the time of day using a microprocessor located in the injection device; and
providing a notification to a patient through a transmitter located in the injection device that instructs the patient to perform the injection at the scheduled injection time of day.

2. The method claim 1, wherein the injection device is configured to accept a cartridge that contains the injectant to be injected into the patient, wherein the cartridge includes an electronically readable marking that includes the information concerning the injectant, further comprising reading an electronically readable marking on a cartridge to obtain the information concerning the injectant.

3. The method of claim 1, further comprising sending information about the injection via the transmitter to a health care provider for monitoring.

4. The method of claim 1, further comprising:
monitoring when the injection is performed using the microprocessor; and
notifying a health care provider via a message sent through the transmitter if the scheduled injection time of day passes without the injection being performed.

5. The method of claim 1, further comprising validating one or more settings of the injection device using the microprocessor prior to injecting the patient using the injector device.

6. The method of claim 1, further comprising determining whether the injection device is properly configured using the microprocessor prior to allowing an injection.

7. The method of claim 6, further comprising disabling the injection device using the microprocessor if the injection device is determined not be properly configured for an injection.

8. The method of claim 1, further comprising:
receiving one or more control signals in the receiver; and
automatically configuring the injection device for an injection using the received control signals.

9. The method of claim 1, further comprising controlling a plunger via the microprocessor to inject an injectant into a patient using the information.

10. The method of claim 9, wherein the injection device includes an actuator and a dosage control, further comprising, controlling the actuator using the microprocessor to rotate the dosage control by an amount sufficient to cause a proper dosage of injectant to be administered to the patient.

11. The method of claim 1, further comprising sending injectant administration data back to a health care provider using the transmitter.

12. The method of claim 1, wherein the injection device includes a memory, further storing injectant administration data in the memory.

13. The method of claim 11, further comprising sending injectant administration data stored in the memory to a health care provider.

14. A method for controlling an injection device, comprising:
reading an electronically readable label on a cartridge placed in the injection device to obtain information concerning an injection, wherein the information includes information concerning the injection to be performed;

monitoring conditions using a microprocessor located in the injection device to determine whether the monitored conditions have been satisfied to perform the injection; and providing a notification to a patient through a transmitter located in the compartment of the injection device that instructs the patient to perform the injection when the conditions required to perform the injection have been met.

15. The method claim 14, wherein the information includes dosage information, further comprising controlling a plunger via the microprocessor to inject an injectant into a patient using the information.

16. The method of claim 14, further comprising sending information about the injection via the transmitter to a health care provider for monitoring.

17. The method of claim 14, wherein the information includes a time of day for performing the injection, further comprising:

monitoring the time of day using the microprocessor;

determining whether the injection was performed at the time of day included in the information using the microprocessor; and notifying a health care provider via a message sent through the transmitter if the scheduled injection time of day passes without the injection being performed.

18. The method of claim 14, further comprising disabling the injection device if the injection device is determined not be properly configured for an injection.

19. The method of claim 14, further comprising sending injectant administration data back to a health care provider using the transmitter.

20. The method of claim 14, further comprising receiving one or more control signals from a health care provider that are used to control the injection.

* * * * *